United States Patent
Li et al.

(10) Patent No.: US 8,003,133 B2
(45) Date of Patent: *Aug. 23, 2011

(54) CALCIUM PHOSPHATE DELIVERY VEHICLES FOR OSTEOINDUCTIVE PROTEINS

(75) Inventors: Rebecca Li, Bedford, MA (US); Howard Seeherman, Cambridge, MA (US); Aliassghar Tofighi, Waltham, MA (US)

(73) Assignees: Wyeth LLC, Madison, NJ (US); Etex Corporation, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/565,159

(22) Filed: Sep. 23, 2009

(65) Prior Publication Data

US 2010/0074876 A1 Mar. 25, 2010

Related U.S. Application Data

(63) Continuation of application No. 11/957,691, filed on Dec. 17, 2007, now Pat. No. 7,622,139, which is a continuation of application No. 10/160,607, filed on May 31, 2002, now Pat. No. 7,413,753.

(60) Provisional application No. 60/296,818, filed on Jun. 8, 2001.

(51) Int. Cl.
 A61K 33/42 (2006.01)
 A61K 33/00 (2006.01)

(52) U.S. Cl. .................. 424/601; 424/717

(58) Field of Classification Search .......... 424/602, 424/717
 See application file for complete search history.

(56) References Cited

U.S. PATENT DOCUMENTS

| | | |
|---|---|---|
| 2,465,357 A | 3/1949 | Correll et al. |
| 3,955,719 A | 5/1976 | Pheulpin |
| 4,159,358 A | 6/1979 | Hench et al. |
| 4,191,747 A | 3/1980 | Scheicher |
| 4,563,489 A | 1/1986 | Urist |
| 4,596,574 A | 6/1986 | Urist |
| 4,758,233 A | 7/1988 | Phillips et al. |
| 4,784,055 A | 11/1988 | Langen et al. |
| 4,851,521 A | 7/1989 | della Valle et al. |
| 5,013,649 A | 5/1991 | Wang et al. |
| 5,024,841 A | 6/1991 | Chu et al. |
| 5,118,667 A | 6/1992 | Adams et al. |
| 5,124,316 A | 6/1992 | Antoniades et al. |
| 5,171,579 A | 12/1992 | Ron et al. |
| 5,256,418 A | 10/1993 | Kemp et al. |
| 5,308,889 A | 5/1994 | Rhee et al. |
| 5,324,519 A | 6/1994 | Dunn et al. |
| 5,324,775 A | 6/1994 | Rhee et al. |
| 5,328,955 A | 7/1994 | Rhee et al. |
| 5,352,715 A | 10/1994 | Wallace et al. |
| 5,356,629 A | 10/1994 | Sander et al. |
| 5,422,340 A | 6/1995 | Ammann et al. |
| 5,447,725 A | 9/1995 | Damani et al. |
| 5,464,440 A | 11/1995 | Johansson |
| 5,492,697 A | 2/1996 | Boyan et al. |
| 5,520,923 A | 5/1996 | Tjia et al. |
| 5,645,592 A | 7/1997 | Nicolais et al. |
| 5,650,176 A | 7/1997 | Lee et al. |
| 5,676,976 A | 10/1997 | Lee et al. |
| 5,752,974 A | 5/1998 | Rhee et al. |
| 5,789,543 A * | 8/1998 | Ingham et al. ............. 530/350 |
| 5,935,594 A | 8/1999 | Ringeisen et al. |
| 5,939,323 A | 8/1999 | Valentini et al. |
| 5,972,368 A | 10/1999 | McKay |
| 6,002,065 A | 12/1999 | Constantz et al. |
| 6,005,162 A | 12/1999 | Constantz |
| 6,077,076 A | 6/2000 | Comfort |
| 6,139,578 A | 10/2000 | Lee et al. |
| 6,699,471 B2 | 3/2004 | Radice et al. |
| 7,413,753 B2 | 8/2008 | Li et al. |
| 2002/0187104 A1 | 12/2002 | Li et al. |
| 2002/0193883 A1 | 12/2002 | Wironen |
| 2008/0096797 A1 | 4/2008 | Li et al. |

FOREIGN PATENT DOCUMENTS

| | | |
|---|---|---|
| EP | 0 058 481 | 8/1982 |
| EP | 0 329 239 | 8/1989 |
| EP | 0 530 804 | 3/1993 |
| JP | 07-0246235 | 9/1995 |
| JP | 11511722 | 10/1999 |
| WO | WO 91/17777 | 11/1991 |
| WO | WO 92/05199 | 4/1992 |
| WO | WO 93/00050 | 1/1993 |
| WO | WO 93/06872 | 4/1993 |
| WO | WO 93/20858 | 10/1993 |
| WO | WO 96/36562 | 11/1996 |
| WO | WO 96/39203 | 12/1996 |
| WO | WO 96/40297 | 12/1996 |
| WO | WO 97/40137 | 10/1997 |
| WO | WO 97/45532 | 12/1997 |
| WO | WO 97/49412 | 12/1997 |
| WO | WO 98/31788 | 7/1998 |
| WO | WO 98/40113 | 9/1998 |

(Continued)

OTHER PUBLICATIONS

Campoccia et al., "Semisynthetic Resorbabel Materials from Hyaluronan Esterification", Biomaterials, 19:2101-27 (1998).
Fleisch, "Bisphosphonates in bone disease, From the Laboratory to the patient", 3rd Ed., Parthenon Publishing (1997).
Gerhart et al., "Healing of Large Mid-Femoral Segmental Defects in Sheep Using Recombinant Human Bone Morphogenetic Protein (BMP-2)", Trans. Othop. Res. Soc., 16:172 (1991).
International Preliminary Examination Report for PCT/US2002/17798, dated Jan. 24, 2003.
International Search Report for PCT/US2002/17798, dated Dec. 17, 2002.
Lee et al., "α-BSM®: A Biomimetic Bone Substitute and Drug Delivery Vehicle", Clin. Orthop. Rel. Res., 367S:S396-S405 (1999).

(Continued)

Primary Examiner — Raymond Henley, III
(74) Attorney, Agent, or Firm — DLA Piper LLP (US)

(57) ABSTRACT

A composition for delivery of osteogenic proteins is disclosed. The composition comprises an osteogenic protein, a calcium phosphate material as a carrier, and an effective amount of an effervescent agent. Methods of making the compositions and methods of using the osteogenic compositions to treat osteoporotic and/or osteopenic bone are also disclosed.

28 Claims, No Drawings

FOREIGN PATENT DOCUMENTS

| | | |
|---|---|---|
| WO | WO 99/24070 | 5/1999 |
| WO | WO 99/38543 | 8/1999 |
| WO | WO 00/37124 | 6/2000 |
| WO | WO 00/45870 | 8/2000 |
| WO | WO 01/28602 | 4/2001 |
| WO | WO 01/28603 | 4/2001 |
| WO | WO 02/058755 | 8/2002 |
| WO | WO 02/100331 | 12/2002 |
| WO | WO 03/099992 | 12/2003 |

OTHER PUBLICATIONS

Leslie M., "Hyaluronic Acid Treatment for Osteoarthritis of the Knee", Nurse Practitioner, 24:38, 41-8 (1999).

Ohura et al., "Resporation of, and Bone Formation From New β-tricalcium Phosphate-Monocalcium Phosphate Cements", J. Biomed. Mat. Res., 30:193-200 (1996).

Ohura et al., "Healing of Segmental Bone Defects in Rats Induced by a β-TCP- MCPM Cement Combined with rhBMP-2", J. Biomed. Mat. Res., 44:168-175 (1999).

Stedman's Medical Dictionary, 25th Ed. p. 38 "air" (1990).

Tona et al., "Extracellular Matrix in Regenerating Rat Sciatic Nerve: A Comparative Study on the Localization of Laminin Hyaluronic Acie, and Chondroitin Sulfate Proteglycans, Including Versican", J. Histochem. Cytochem., 41:591-599 (1993).

Toriumi et al., "Mandibular Reconstruction With a Recombinant Bone-Inducing Factor", Arch. Otolaryngol. Head Neck Surg., 117:1101-1112 (1991).

Urist et al., "β-tricalcium Phosphate Delivery System for Bone Morphogenetic Protein", Clin. Orthoped. Rel. Res., 187:277-280 (1984).

Urist et al., "Clinical Orthopaedics and Related Research", Clin. Orthoped. Rel. Res., 214:295-304 (1986).

Urist et al., "Bone Morphogenisis in Implants of Insoluble Bone Gelatin", PNAS, 70:3511 (1973).

Wang, E. E., "Bone Morphognetic Protein-2 Causes Commitment and Differentiation in C3H10T1/2 and 3T3 Cells", Trends in Biotech., 11:379-383 (1993).

Blom et al., "Transforming growth factor-β1 incorporated during setting in calcium phosphate cement stimulates bone cell differentiation in vitro," *Journal of Biomedical Materials Research*, vol. 50, No. 1, pp. 67-74 (2000).

Leroux et al., "Effects of Various Adjuvants (Lactic Acid, Glycerol, and Chitosan) on the injectability of a calcium phosphate cement," *Bone*, vol. 26, No. 2, pp. 31S-34S (1999).

Otsuka et aL, "Effect of Sodium Bicarbonate Amount on In Vitro indomethacin release from self-setting carbonated-apatite cement" *Pharmaceutical Research*, vol. 14, No. 4, pp. 444-449 (1997).

European Search Report dated Nov. 3, 2010, in corresponding EP Application No. 10183027.1.

\* cited by examiner

CALCIUM PHOSPHATE DELIVERY VEHICLES FOR OSTEOINDUCTIVE PROTEINS

This application is a continuation of application Ser. No. 11/957,691, filed on Dec. 17, 2007, now U.S. Pat. No. 7,622,139, issued on Nov. 24, 2009, which is a continuation of application Ser. No. 10/160,607, filed on May 31, 2002, now U.S. Pat. No. 7,413,753 issued on Aug. 19, 2008 claims the benefit of U.S. provisional application No. 60/296,818, filed Jun. 8, 2001, all of which are incorporated herein by reference.

This invention relates to composite materials containing calcium phosphate useful as delivery vehicles for osteoinductive proteins. The invention further relates to biocompatible, osteoinductive composites that can be used for bone regeneration and osseous augmentation, as well as for tissue repair and reinforcement in bone fractures, dental implants, bone implants and prostheses and the like.

Much research in the area of biopharmaceutics is directed toward the development of effective implantable vehicles for drug delivery and other surgical applications. Such vehicles must be biocompatible and also must be capable of protecting the activity of any biologically active agent they are intended to deliver. Many biologically active agents are labile and easily lose activity when they are incorporated into a delivery material. Preservation of protein activity has posed particularly difficult problems.

In the drug delivery arena, calcium phosphate ceramics have been studied as potential delivery vehicles due to their well known biocompatibility and their affinity for protein reagents (see, e.g., Ijntema et al, *Int. J. Pharm.* 112:215 (1994); Itokazu et al., *J. Orth. Res.* 10:440 (1992); Shinto et al., *J. Bone Joint Surg.* 74-B:600 (1992); and Uchida et al., *J. Orth. Res.* 10:440 (1992)). Most of these materials have been in the form of prefabricated, sintered hydroxyapatite in either granule or block forms. These preparations have several drawbacks, including a limited ability to conform to skeletal defects, particularly in the case of blocks; inadequate structural integrity of granules (which do not bond together); and difficulty in modeling the implant to the shape of missing skeletal tissue with both blocks and granules. The block form of hydroxyapatite provides structural support, but among other complications, must be held in place by mechanical means, which greatly limits its use and its cosmetic results. Also, it is very difficult to saw a hydroxyapatite block into a shape that fits the patient's individual defect. The granular form produces cosmetically better results, but has a very limited structural stability and is difficult to contain during and after a surgical procedure. In general, all of these products are ceramics, produced by high temperature sintering, and are not individually crystalline, but rather have their crystal boundaries fused together. Most ceramic-type materials are in general functionally biologically non-absorbable (having an absorption rate generally not exceeding on the order of 1% per year).

A porous, non-resorbable material based on coral allows intergrowth with bone, but ultimately becomes only approximately 20% bone with the remaining 80% subsisting as scar tissue. HA RESORB® made by Osteogen is a form of absorbable hydroxyapatite, but is not a cement. It is granular and not adhesive. HA RESORB® is loosely rather than adhesively packed into place. For large uses, it is replaced by bone too quickly. In the dental materials market, HAPSET® is a composition of calcium phosphate granules and cementable plaster of Paris (calcium sulfate). This material is not truly a hydroxyapatite and contains too much calcium sulfate for most biological uses. The calcium sulfate component of such a composition is resorbable, but not the calcium phosphate granules.

At least one class of calcium phosphate compositions are precursors for the formation of hydroxyapatite and are biologically compatible, and have two unique properties that are not attainable in other calcium phosphate biomaterials: (1) self-hardening to form a mass with sufficient strength for many medical and dental applications, and (2) when implanted in bone, the material resorbs slowly and is completely replaced by new bone formation with no loss in the volume or integrity of the tissue that receives the implant. See U.S. Pat. Nos. Re. 33,221 and Re. 33,161 to Brown and Chow, which teach preparation of calcium phosphate remineralization compositions and of a finely crystalline, non-ceramic, gradually resorbable hydroxyapatite material based on the same calcium phosphate composition.

A virtually identical calcium phosphate system, which consists of tetracalcium phosphate (TTCP) and monocalcium phosphate (MCP) or its monohydrate form (MCPM) was described by Constantz et al. (U.S. Pat. Nos. 5,053,212 and 5,129,905). This system reportedly involves conversion of the MCP to dicalcium phosphate, which reacts with TTCP and forms hydroxyapatite (HA), the major mineral component of teeth and bone, as the end product.

Another type of calcium phosphate composition comprises an amorphous, apatitic calcium phosphate as a reactant, a promoter, and an aqueous liquid to form a hardening paste. See, e.g., U.S. Pat. Nos. 5,650,176; 5,676,976; 5,683,461; 6,027,742; and 6,117,456 to Lee et al. This system provides a bioactive ceramic material that is biocompatible, bioresorbable and workable for long periods of time at room temperature. The bioactive ceramic material may be formed at low temperatures, is readily formable and/or injectable, and yet can harden to high strength upon further reaction. The bioactive ceramic material contains poorly crystalline apatitic calcium phosphate solids with calcium-to-phosphate (Ca/P) ratios comparable to naturally occurring bone minerals and having stiffness and fracture roughness similar to natural bone. The bioactive ceramic composite material is strongly bioresorbable and its biosorbability and reactivity can be adjusted to meet the demands of the particular therapy and/or implant site. The material may be prepared as bone plates, bone screws and other fixtures and medical devices, including veterinarian applications, which are strongly bioresorbable and/or ossifying.

One of the goals of reconstructive surgery is to be able to replace damaged tissue with new tissue, using either a patient's own cells or growth enhancing proteins. For example, researchers have endeavored to develop cartilage regeneration systems in which isolated chondrocytes are injected into a damaged area in the context of a polymer scaffold (see, e.g., Atala et al., *J. Urol.* 150:747 (1993); Freed et al., *J. Cell. Biochem.* 51:257 (1993) and references cited therein). Similar seeded scaffold systems have been studied in the context of bone repair, where osteoblast cells are utilized in conjunction with polymeric or ceramic supports (see, e.g., Elgendy et al., *Biomater.* 14:263 (1993); Ishaug et al., *J. Biomed. Mater. Res.* 28:1445 (1994)). Of particular interest are osteoinductive materials such as bone morphogenetic proteins (e.g., recombinant human BMP-2), demineralized bone matrix; transforming growth factors (e.g., TGF-β); and various other organic species known to induce bone formation.

Three general types of calcium phosphate-based scaffold materials have been designed specifically for use with seeded compositions. One type of scaffold material consists of preformed calcium phosphate-based granules with the bioactive substance bound on the external surface. In general, large granules (ideally 100-1000 µm) are required to avoid eliciting inflammatory responses. However, such large pre-fabricated granules are not easily injectable through small gauge needles required for percutaneous injection. In addition, factors can only be admixed with preformed granules resulting in surface coating rather than the factor being embedded or dispersed throughout the matrix. Embedding the factor allows for a more controlled release of biomolecules as the matrix is resorbed. Pre-formed granules are typically difficult to handle and apply. Furthermore, most pre-formed hydroxyapatite granules are produced by a sintering process rendering them essentially non-resorbable.

A second type of scaffold material for seeded compositions consists of implantable porous hydroxyapatite or tricalcium phosphate blocks. Implantable porous blocks may be prepared with varying degrees of porosity, typically using a dry mixture of controlled particle size reactants. Other methods of promoting porosity include chemical or physical etching and leaching. Although they generally provide sufficient support, porous blocks have several significant drawbacks. First, like the pre-fabricated granules described above, block scaffolds do not have the osteoinductive substance embedded throughout the volume, and thus prevent controlled release of the active substance. Second, implantable blocks are not injectable, and thus require a more intrusive implantation procedure. Finally, and importantly, monolithic blocks may impede the rate of bone formation for clinical applications where an acceleration of healing is desired over the normal time course of healing. This delay may be due to slow resorption of the solid carrier and subsequent delayed release of the active substance. The presence of the monolithic matrix may also obstruct cell migration and infiltration to the fracture site. Assuming the block matrix contains interconnecting channels between the pores, new bone growth will be dictated by the pores and bounds of the scaffold walls, thus limiting new bone formation.

A third type of scaffold material involves calcium phosphate cements. Unlike the prefabricated granules and monolithic blocks, cements are readily injectable and can have the osteoinductive substance embedded throughout the volume. However, these cements tend to form monolithic aggregates that are inherently microporous. Although macroporous versions using biodegradable pore-formers have been described (see, e.g., PCT publication No. WO 98/16209, which is incorporated herein by reference), these cements form monolithic scaffolds which contain channels rather than microporous granules which, as discussed above, significantly restricts new bone growth.

Accordingly, despite substantial endeavors in this field, there remains a need for a drug delivery vehicle that is biocompatible, readily resorbable, and not detrimental to drug activity. Ideally, the vehicle should be injectable; malleable to enable injection or implantation into various sized fractures and defects; promote homogeneous distribution of bioactive materials throughout the matrix, thus permitting controlled release of the active substance; and, finally, form discrete macrogranules upon administration to the surgical or defective site. Granulation is desirable to facilitate cell migration and infiltration for secretion of extracellular bone matrix, and to provide access for vascularization. Granules also provide high surface area for enhanced resorption and release of active substance, as well as increased cell-matrix interaction. The present invention solves these needs, providing materials and compositions useful in drug delivery and in tissue repair.

In one embodiment, the invention provides a composition for delivery of osteogenic proteins, comprising a calcium phosphate material, an effective amount of an effervescent agent, and a biologically active agent. The calcium phosphate material may be an amorphous apatitic calcium phosphate, hydroxyapatite, tricalcium phosphate, or fluorapatite. In a preferred embodiment, the calcium phosphate material is an amorphous apatitic calcium phosphate, for example a poorly crystalline apatitic calcium phosphate. The poorly crystalline apatitic calcium phosphate may have a calcium-to-phosphate (Ca:P) ratio comparable to naturally occurring bone minerals. In preferred embodiments, the Ca:P ratio is less than 1.5, preferably about 1.4. The osteogenic protein may be a member of the bone morphogenic protein (BMP) family, including BMP-2, BMP-4, BMP-5, BMP-6, BMP-7, BMP-10, BMP-12 and BMP-13. In a preferred embodiment, the osteogenic protein is BMP-2 or BMP-6. The effervescent agent may be gas selected from the group consisting of carbon dioxide, air, nitrogen, helium, oxygen, and argon. In a preferred embodiment, the effervescent is sodium bicarbonate. The sodium bicarbonate may be present at a concentration of between about 10 and about 40 percent (w/w). The composition may further comprise one or more supplementary materials, such as pharmaceutically acceptable salts, polysaccharides, peptides, proteins, amino acids, synthetic polymers, natural polymers, and surfactants; solid structures, such as sponges, meshes, films, fibers, gels, filaments, microparticles, and nanoparticles; bioerodible polymers, such as collagen, glycogen, chitin, celluloses, starch, keratins, silk, nucleic acids, demineralized bone matrix, derivativized hyaluronic acid, polyanhydrides, polyorthoesters, polyglycolic acid, polylactic acid, and copolymers and derivates thereof; alpha-hydroxycarboxylic acids, such as poly(L-lactide) (PLLA), poly(D,L-lactide) (PDLLA), polyglycolide (PGA), poly(lactide-co-glycolide) (PLGA), poly(D,L-lactide-co-trimethylene carbonate), and polyhydroxybutyrate (PHB), and polyanhydrides, and co-polymers and derivatives thereof; $SiO_2$, $Na_2O$, $CaO$, $P_2O_5$, $Al_2O_3$ and $CaF_2$, and polysaccharides, peptides and fatty acids. The composition may further comprise a second active agent, such as a Hedghog, Frazzled, Chordin, Noggin, Cerberus and Follistatin protein.

In another aspect, the invention relates to method of treating a mammal having a bone defect comprising administering to the site of bone defect an effective amount of an osteogenic composition, wherein the osteogenic composition comprises a bone morphogenetic protein, a calcium phosphate material, and an effervescent agent. In a preferred embodiment, the effervescent agent is sodium bicarbonate.

The present invention is directed to osteoinductive compositions adapted for use in the repair, regeneration and augmentation of bone tissue. The composition comprises a biocompatible and bioresorbable calcium phosphate material, an effervescent agent, and a biologically active agent. Upon hardening, the calcium phosphate material provides a resorbable scaffold for new bone growth. The effervescent agent prevents the calcium phosphate from forming a unitary monolithic structure by facilitating the formation of discrete macrogranules, which disperse during hardening of the calcium phosphate. The biologically active agent stimulates increased osteogenic activity of present or infiltrating progenitor or other cells. The osteoinductive compositions are useful for osseous augmentation and regeneration of bone tissue, for example in osteopenic bone, as well as for tissue repair and reinforcement in bone fractures, dental implants, bone implants and prostheses and the like.

As used herein, a "calcium phosphate material" means a synthetic bone substitute material comprising calcium phosphate as the primary component. Suitable calcium phosphate-based materials are well known in the art and include, without limitation, amorphous apatitic calcium phosphate, hydroxyapatite, tricalcium phosphate, and fluorapatite. In a preferred embodiment, the calcium phosphate material is a poorly crystalline apatitic calcium phosphate solid having a calcium-to-phosphate (Ca/P) ratio comparable to naturally occurring bone minerals. Such materials may be produced using a combination of amorphous, apatitic calcium phosphate as a reactant, a promoter, and an aqueous liquid to form a hardening paste. In an alternative embodiment, the calcium phosphate material is produced by solid-state acid-base reaction of crystalline calcium phosphate reactants to form crystalline hydroxyapatite solids.

"Effervescent agent" refers to a gaseous substance or a substance, which produces bubbling, foaming or liberation of a gas.

As used herein, "amorphous" means a material with significant amorphous character. Significant amorphous character contemplates greater than 75% amorphous content, preferably greater than 90% amorphous content, and is characterized by a broad, featureless X-ray diffraction pattern.

"Bioactive" refers to a material that induces hard tissue formation in and about the implant. When implanted in soft tissue, the bioactivity may also require the presence of a growth or trophic factor, or the seeding of the implant with a hard tissue forming cell type.

The term "biocompatible," as used herein, means that the material does not elicit a substantial detrimental response in the host. There is always concern, when a foreign object is introduced into a living body, that the object will induce an immune reaction, such as an inflammatory response that will have negative effects on the host. For example, although hydroxyapatite is generally considered to be "biocompatible," significant inflammation and tissue necrosis have been observed when crystalline hydroxyapatite microcarriers are inserted intramuscularly in animals (see, for example, IJntema et al., *Int. J. Pharm.* 112:215 (1994)).

"Bioresorbable" refers to the ability of a material to be resorbed in vivo. The resorption process involves elimination of the original implant materials through the action of body fluids, enzymes or cells. Resorbed calcium phosphate may, for example, be redeposited as bone mineral, or by being otherwise reutilized within the body, or excreted. "Strongly bioresorbable," as that term is used herein, means that at least 80% of the total mass of material implanted intramuscularly or subcutaneously is resorbed within one year. In preferred embodiments, the material will be resorbed within nine months, six months, three months, and ideally one month.

An "effective amount" of an effervescent agent is an amount sufficient to effect the formation of macrogranules upon hardening, and will depend upon the calcium phosphate material being used. Generally, the amount of effervescent agent is added in a range of from about 1 to 90 percent by weight, preferably about 1 to 50 percent by weight, and more preferably about 10 to 40 percent by weight.

As used herein, a "macrogranule" means a granule or particle of between about 100 microns and 1 millimeter in diameter. The macrogranular material formed upon hardening of the inventive calcium-phosphate composition is biocompatible (i.e., the macrogranules are of sufficient size to avoid eliciting an inflammatory response) and macroporous, as described below.

As used herein, "macroporous" refers to a hardened calcium phosphate material having pores of sufficient diameter to permit cell migration and infiltration. In a preferred embodiment, the macroporous material formed in accordance with the present invention has a pore diameter of greater than 30 microns, more preferably between about 30 and 200 microns, and most preferably between about 50 and 100 microns in diameter. The macroporous material of the present invention facilitates cell migration and infiltration for secretion of extracellular bone matrix, as well as enhancing cell-matrix interactions.

An "effective amount" of a biologically active agent is an amount sufficient to stimulate increased osteogenic activity of present or infiltrating progenitor or other cells. The amount will depend upon the size and nature of the defect being treated, as well as the composition of the calcium phosphate material being employed. Generally, the amount of biologically active agent to be delivered is in a range of from about 0.1 to about 100 mg; preferably about 1 to about 100 mg; and most preferably about 10 to about 80 mg.

An "effective amount" of a supplemental material is an amount sufficient to impart the desired mechanical or chemical property to the composite.

"Hardening" refers to the process by which the malleable calcium phosphate composition is transformed into a hardened calcium phosphate material. The calcium phosphate material is considered to be "hardened" when it is a substantially non-formable solid. Such a hardened calcium phosphate material has minimal compressibility and tends to undergo plastic as opposed to elastic deformation.

"Poorly crystalline apatitic calcium phosphate," "PCA calcium phosphate" and "PCA material," as those terms are used herein, describe a synthetic poorly crystalline apatitic calcium phosphate. The poorly crystalline apatitic (PCA) material is not necessarily restricted to a single calcium phosphate phase provided it has the characteristic X-ray diffraction (XRD) and FTIR pattern. A PCA calcium phosphate has substantially the same XRD spectrum as bone. The spectrum is generally characterized by only two broad peaks in the region of 20-35° with one centered at 26° and the other centered at 32°, and by FTIR peaks at 563 $cm^{-1}$, 1034 $cm^{-1}$, 1638 $cm^{-1}$ and 3432 $cm^{-1}$ (±2 $cm^{-1}$). Sharp shoulders are observed at 603 $cm^{-1}$ and 875 $cm^{-1}$, with a doublet having maxima at 1422 $cm^{-1}$ and 1457 $cm^{-1}$.

"Hydrated precursor," as used herein, refers to the paste or putty formed by hydration of the dry PCA precursors in the presence of a limited amount of aqueous solution (i.e., less than approximately 1 mL aqueous solution/1 g precursor powder). The hydrated precursor may comprise both reactants and products, in various combinations, depending on the extent to which the conversion has progressed. Both the "injectable" and "formable" PCA precursor pastes described herein are hydrated precursors. Preferred "injectable" hydrated precursors have a consistency appropriate for delivery through an 18-gauge hypodermic needle.

The term "promoter," as used herein, describes a material or treatment that promotes hardening of a hydrated precursor and may enhance the amorphous calcium phosphate (ACP) to PCA calcium phosphate conversion. Some promoters participate in the conversion and are incorporated into the PCA material; others, known as "passive" promoters, are not involved in the conversion.

"Reactive" is used herein to refer to the ability of a calcium phosphate, when mixed with liquid to form a hydrated precursor, to undergo conversion to the PCA material in the presence of a promoter in association with hardening of the precursor materials. Preferred ACPs are characterized by an ability to convert completely, an ability to convert quickly with hardening, an ability to undergo conversion with otherwise inert compounds and/or an ability to convert into a substantially homogeneous PCA material. Where the ACP is reacted with a second calcium phosphate, the "conversion"

can encompass conversion of both the ACP and the second calcium phosphate. The degree of hardening and the kinetics of the hardening process are also important elements of reactivity. Some ACPs are more reactive than others. An ACP is considered "highly reactive" if it undergoes conversion and hardening to a PCA material in the presence of a weak promoter, such as dicalcium phosphate dihydrate (DCPD). Preferred highly reactive ACPs produce a hardened PCA material in the presence of weakly promoting DCPD and water at 37° C. in less than twelve hours, with hardening being substantially complete in about one to five hours, and ideally 10-30 minutes.

The Calcium Phosphate Material

Calcium phosphate component of the present invention may be any biocompatible, calcium phosphate material known in the art. The calcium phosphate material may be produced by any one of a variety of methods and using any suitable starting components. For example, the calcium phosphate material may be produced using a combination of amorphous, apatitic calcium phosphate as a reactant, a promoter, and an aqueous liquid to form a hardening paste. Alternatively, the calcium phosphate material may be produced by solid-state acid-base reaction of crystalline calcium phosphate reactants to form crystalline hydroxyapatite solids. Other methods of making calcium phosphate matrix materials are known in the art.

Poorly Crystalline Apatitic (PCA) Calcium Phosphate

In one embodiment, the calcium phosphate material is poorly crystalline apatitic (PCA) calcium phosphate. PCA material is described in application U.S. Ser. No. 08/650,764 and U.S. Pat. No. 5,650,176, both of which are hereby incorporated by reference in their entireties herein. The material is also described in a set of related applications, entitled "Delivery Vehicle," "Conversion of Amorphous Calcium Phosphate to Form a Novel Bioceramic," "Orthopedic and Dental Ceramic Implants," and "Bioactive Ceramic Composites," each of which was filed on Oct. 16, 1997 and assigned to ETEX Corporation (Cambridge, Mass.) and is incorporated herein by reference. In light of the breadth of disclosures in each of these related applications, the details of the PCA materials will not be belabored here. A summary of its characteristics will suffice.

The PCA material is characterized by its biological resorbability and its minimal crystallinity. Its crystalline character is substantially the same as natural bone. PCA material also is biocompatible and not detrimental to the host.

The PCA material may be implanted in a patient in a paste or putty form (i.e., as a hydrated precursor). Since the inventive reaction that produces the homogenous, macroporous calcium phosphate material can be initiated outside the body, and proceeds slowly at room temperature, the possibility that the material will "set up" prior to application to the surgical site and become unusable is minimized. The reaction accelerates significantly under physiological conditions (i.e., body temperature and pressure) and the material hardens in place. This feature is particularly useful in the surgical setting, where custom fitting of the device to the implant location is typically required. For example, the PCA paste containing the effervescent agent and biologically active agent may be applied to and used to fill a fracture site.

Alternatively, the PCA material may be pre-hardened outside the body, loaded with the desired biologically active agent and effervescent agent, and implanted at a later time. This approach is useful in those situations where custom shapes are not essential, and where production of large numbers of implants is desired.

Generally, the formation reaction of the present invention is completed after application to the surgical site. The material typically hardens in less than five hours, and substantially hardens in about one to five hours, under physiological conditions. Preferably, the material is substantially hardened within about 10-30 minutes. The consistency and formability of the PCA material, as well as the speed of the formation reaction, may be varied according to the therapeutic need by modifying a few simple parameters (see, e.g., U.S. Pat. No. 6,027,742 to Lee et al, which is incorporated by reference in its entirety herein).

The conversion reaction that produces the PCA material may be initiated by adding distilled water to a mixture of the dry precursor components to form a thick hydrated precursor in the form of a paste or putty. Other aqueous agents such as buffers, saline, serum or tissue culture medium may be used in place of distilled water. In other embodiments, sufficient water may be added to the precursor powders to form a paste, which, upon addition of the other invention components, is readily injectable with an 18 gauge needle. Most often, the resulting bioresorbable calcium phosphate material will be "calcium deficient," with a calcium to phosphate ratio of less than 1.5 as compared to the ideal stoichiometric value of approximately 1.67 for hydroxyapatite.

Suitable PCA materials may be identified by combining the PCA precursors, hydrating with a limited amount of water (so that a paste or putty is formed), and allowing to harden into a PCA material. Desirable precursors are capable of hardening in a moist environment, at or around body temperature in less than 5 hours and preferably within 10-30 minutes. Components which harden in this way may then be placed intramuscularly or subcutaneously in a test animal and checked for biological resorbability. Desirable materials are those that, when implanted as a 1-5 g pellet, are at least 80% resorbed within one year. Preferably, the material can be fully resorbed. Generally, it is easier to test resorption of gram quantities of material in subcutaneous sites.

The PCA material may be formed in a reaction that employs at least one amorphous calcium phosphate (ACP) precursor, and preferably employs an activated or reactive ACP (see, e.g., PCT application No. WO 98/16209; Examples 1-4). In some instances, the reaction may employ only one precursor ACP, which is converted in a controlled fashion in part or whole to the PCA material. Also, a non-participating promoter may be employed to facilitate conversion of the activated ACP to the PCA material. In any event, reactions that can be initiated outside of the body, that can be carried out in a paste-like configuration, and that significantly accelerate at 37° C. leading to a hardened calcium phosphate product are greatly preferred.

The conversion of ACP to PCA material is promoted in the presence of water. Generally, the ACP is provided as a powder and combined with any other reactants (e.g., a second calcium phosphate), and is exposed to a limited amount of water, so that a past or putty is formed. The hydrated precursor then hardens, and the hardening is associated with formation of the PCA material. The conversion of ACP to PCA calcium phosphate proceeds in a controlled fashion as a paste or putty which hardens predictably and which has utility in dental, orthopedic, or other therapeutic applications.

When amorphous calcium phosphate is used as the sole precursor to produce a resorbable PCA material, it is important to control the natural tendency of the ACP to convert to highly crystalline hydroxyapatite. On the other hand, the time course of conversion should be fast enough to have surgical utility. One approach is to combine a precursor ACP containing an inhibitor of crystal formation (see, e.g., WO 98/16209;

Example 1) with an ACP that does not contain an inhibitor of crystal formation (e.g., a promoter). The reactants may be mixed in a dry state, with the appropriate particulate size and an excess of the inhibitor-containing ACP. The reactants can then be hydrated by addition of water, followed by an elevation in temperature (e.g., as occurs following introduction into the body), to convert the reactants to the PCA material. Other methods of controlled conversion involve the use of catalysts.

Crystalline Hydroxyapatite

In a second embodiment, the calcium phosphate material is crystalline hydroxyapatite (HA). Crystalline HA is described, for example, in U.S. Pat. Nos. Re. 33,221 and Re. 33,161 to Brown and Chow, both of which are herein incorporated by reference. The Brown and Chow patents teach preparation of calcium phosphate remineralization compositions and of a finely crystalline, non-ceramic, gradually resorbable hydroxyapatite carrier material based on the same calcium phosphate composition. A similar calcium phosphate system, which consists of tetracalcium phosphate (TTCP) and monocalcium phosphate (MCP) or its monohydrate form (MCPM), is described by Constantz et al. in U.S. Pat. Nos. 5,053,212 and 5,129,905, both of which are incorporated herein by reference. In this embodiment, the calcium phosphate material is produced by solid-state acid-base reaction of crystalline calcium phosphate reactants to form crystalline hydroxyapatite solids.

Crystalline HA materials (commonly referred to as dahllite) may be prepared such that they are flowable, moldable, and capable of hardening in situ (see U.S. Pat. No. 5,962,028 to Constantz). These HA materials (commonly referred to as carbonated hydroxyapatite) can be formed by combining the wet and dry reactants to provide a substantially uniform mixture, shaping the mixture as appropriate, and allowing the mixture to harden. Alternatively, precursor reaction mixtures can be administered to the surgical site and hardened and/or shaped in situ. During hardening, the mixture crystallizes into a solid and essentially monolithic apatitic structure.

The reactants will generally consist of a phosphoric acid source substantially free of unbound water, an alkali earth metal, particularly calcium, source, optionally crystalline nuclei, particularly hydroxyapatite or calcium phosphate crystals, calcium carbonate, and a physiologically acceptable lubricant, such as water, which may have various solutes. The dry ingredients may be pre-prepared as a mixture and subsequently combined with the liquid ingredients under conditions where substantially uniform mixing occurs.

The phosphoric acid source may be any partially neutralized phosphoric acid, particularly up to and including complete neutralization of the first proton as in calcium phosphate monobasic. Alternatively or additionally, it can consist of orthophosphoric acid, possibly in a crystalline form, that is substantially free of uncombined water. Calcium sources will generally include counterions such as carbonate, phosphate or the like, particularly dual sources of calcium phosphate and phosphate such as tetracalcium phosphate or tricalcium phosphate.

The various dry components may be combined prior to the addition of the wet components. Mixing combines the ingredients and can be used to regulate the extent of the inter-ingredient reactions. Any or all of the dry ingredients may be added prior to the initiation of mixing or prior to the completion of mechanical mixing. After mixing, the mixture is allowed to anneal while remaining quiescent, followed by an extended period of time during which the mixture hardens.

The Effervescent Agent

The present invention provides a novel process for producing a calcium phosphate matrix or scaffold material which "self-granulates" and disperses into hardened macrogranules or macroparticles under physiological conditions (i.e., post-administration). The calcium phosphate material may be any biocompatible, calcium phosphate material known in the art, such as the PCA calcium phosphate and crystalline hydroxyapatite materials described above. Surprisingly, the present inventors have discovered that the addition of an effervescent agent to these calcium phosphate materials substantially alters the biological, chemical and mechanical properties of the material, thereby significantly enhancing its therapeutic utility. The effervescent agent of the present invention may be any pharmaceutically acceptable substance which produces bubbling or liberation of a gas at physiological temperatures and/or pressures.

All of the currently available methods for producing calcium phosphate materials for use with seeded compositions suffer from certain inherent drawbacks, including limited injectability due to granule formation during production or preparation for administration in the syringe. Pre-fabricated calcium phosphate granules, to which the bioactive substance adheres, must be large (ideally 100-1000 μm) to avoid eliciting inflammatory responses. However, such large pre-fabricated granules are not easily injectable through small gauge needles required for percutaneous injection. Moreover, these granules are typically difficult to handle and apply, and many are produced by a sintering process rendering them essentially non-resorbable. In addition, the active agent can only be admixed with preformed granules resulting in surface coating, rather than being evenly embedded or dispersed throughout the material. Dispersion allows for a more controlled release of biomolecules as the matrix is resorbed.

In an important aspect of the invention, the ease of use of the inventive bioceramic material in a surgical setting is significantly improved over other bone substitute composite materials known in the art. Specifically, an effervescent agent is added to the other components of the composition (e.g., calcium phosphate material and any supplementary materials) to cause gas foaming or bubbling under specific conditions (i.e., physiological temperatures and/or pressures). The bubbling or effervescence induces granulation and dispersion of the calcium phosphate material upon injection or implantation in vivo. As the hardening and/or cement reaction proceeds, granulation occurs simultaneously and the active agent (which may be admixed with the other components or added to the mixture just prior to administration) is homogeneously dispersed throughout the volume of the individual granules.

The effervescent agent is added in an appropriate amount to prevent the formation of a monolithic calcium phosphate mass. The effervescent agent reacts quickly and completely with a wide variety of calcium phosphates and other calcium- or phosphorus-bearing materials to provide a homogeneous injectable delivery vehicle. Depending upon the particular calcium phosphate material, the effervescent agent is selected to sufficiently interfere with the hardening or cementing process to allow the formation of relatively uniform granules, but not to the extent that it renders calcium phosphate cement "non-reactive." The addition of the effervescent agent causes substantial granulation to occur only after injection or implantation in vivo. As a result, granulation does not occur during the preparation of the calcium phosphate material and/or formulation of the cement prior to injection or implantation. Granules formed in the presence of an effervescent agent are sufficiently large to prevent an inflammatory reaction (typically greater than 30 μm), yet small enough to provide a significant surface area to volume ratio. The large surface area to volume ratio enables rapid resorption of the calcium phosphate material as new bone is regenerated. The large surface area also facilitates release of the biologically active agent, while still retaining the agent at the surgical site for the appropriate length of time required for bone induction. In addition, the large surface area to volume ratio facilitates cell migration and infiltration into the matrix for secretion of extracellular bone matrix, as well as providing access for vascularization. Granules formed in vivo using the methods and compositions of the present invention are in the 1-2000 µm range, preferably in the 30-1000 µm range, more preferably in the 30-500 µm range, and most preferably in the 50-100 µm range.

In one embodiment, the effervescent agent is a gas which is dissolved in the hydrated calcium phosphate material. The gas may be dissolved in the material under pressure, i.e., by subjecting the composite material to a pressurized atmosphere of the gas, but which is inert to the cementing reaction. The gas is then liberated upon exposure to physiological temperatures (i.e., upon injection or implantation), due to the decrease in gas solubility with increased temperature. Under these circumstances, the gas dissolution and subsequent granulation occurs only during hardening in vivo, and not prior to administration. This is especially attractive since granulation is not desired to occur at room temperature in the syringe. By way of example only, suitable gases include carbon dioxide, air, nitrogen, helium, oxygen, and argon.

In another embodiment, the effervescent agent is a volatile liquid which vaporizes at physiological temperatures.

In yet another embodiment, the effervescent agent is a solid material which liberates gas upon dissolution. For example, sodium bicarbonate evolves carbon dioxide gas as it converts to an unstable carbonic acid intermediate, which subsequently evolves carbon dioxide and water.

Biologically Active Agents

Any biologically useful agent that facilitates or stimulates new bone growth may be delivered from the inventive calcium phosphate material. Of particular interest are osteoinductive materials such as bone morphogenetic proteins (e.g., recombinant human BMP-2), demineralized bone matrix, transforming growth factors (e.g., TGF-β), and various other organic species known to induce bone formation. Alternatively or in addition, in order to optimize ossification, the delivery vehicle may be seeded with bone forming cells.

Osteoinductive Proteins

The biologically active agent is preferably selected from the family of proteins known as the transforming growth factors-beta (TGF-β) superfamily of proteins, which includes the activins, inhibins and bone morphogenetic proteins (BMPs). Most preferably, the active agent includes at least one protein selected from the subclass of proteins known generally as BMPs, which have been disclosed to have osteogenic activity, and other growth and differentiation type activities. These BMPs include BMP proteins BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in PCT application WO94/26893; BMP-11, disclosed in PCT application WO94/26892, or BMP-12 or BMP-13, disclosed in PCT application WO 95/16035; BMP-15, disclosed in U.S. Pat. No. 5,635,372; or BMP-16, disclosed in U.S. Pat. No. 5,965,403. Other TGF-β proteins which may be useful as the active agent in the present invention include Vgr-2, Jones et al., *Mol. Endocrinol.* 6:1961-1968 (1992), and any of the growth and differentiation factors [GDFs], including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO93/16099. The disclosures of all of the above applications are hereby incorporated by reference. A subset of BMPs which are presently preferred for use in the present invention include BMP-2, BMP-4, BMP-5, BMP-6, BMP-7, BMP-10, BMP-12 and BMP-13. The active agent is most preferably BMP-2, the sequence of which is disclosed in U.S. Pat. No. 5,013,649, the disclosure of which is hereby incorporated by reference. Other BMPs and TGF-β proteins known in the art can also be used.

The active agent may be recombinantly produced, or purified from a protein composition. The active agent, if a TGF-β such as a BMP, or other dimeric protein, may be homodimeric, or may be heterodimeric with other BMPs (e.g., a heterodimer composed of one monomer each of BMP-2 and BMP-6) or with other members of the TGF-β superfamily, such as activins, inhibins and TGF-β1 (e.g., a heterodimer composed of one monomer each of a BMP and a related member of the TGF-β superfamily). Examples of such heterodimeric proteins are described for example in Published PCT Patent Application WO 93/09229, the specification of which is hereby incorporated herein by reference.

The active agent may further comprise additional agents such as the Hedgehog, Frazzled, Chordin, Noggin, Cerberus and Follistatin proteins. These families of proteins are generally described in Sasai et al., *Cell* 79:779-790 (1994) (Chordin); PCT Patent Publication WO94/05800 (Noggin); and Fukui et al., *Devel. Biol.* 159:131-139 (1993) (Follistatin). Hedgehog proteins are described in WO96/16668; WO96/17924; and WO95/18856. The Frazzled family of proteins is a recently discovered family of proteins with high homology to the extracellular binding domain of the receptor protein family known as Frizzled. The Frizzled family of genes and proteins is described in Wang et al., *J. Biol. Chem.* 271:4468-4476 (1996). The active agent may also include other soluble receptors, such as the truncated soluble receptors disclosed in PCT patent publication WO95/07982. From the teaching of WO95/07982, one skilled in the art will recognize that truncated soluble receptors can be prepared for numerous other receptor proteins. Such would also be encompassed within the present invention. The above publications are hereby incorporated by reference herein.

The amount of active agent useful herein is that amount effective to stimulate increased osteogenic activity of present or infiltrating progenitor or other cells, and will depend upon the size and nature of the defect being treated, as well as the carrier being employed. Generally, the amount of protein to be delivered is in a range of from about 0.1 to about 100 mg; preferably about 1 to about 100 mg; most preferably about 10 to about 80 mg.

Bone Forming Cells

In one embodiment, in order to optimize ossification, the calcium phosphate composition may be seeded with bone forming cells, such as progenitor cells, stem cells, and/or osteoblasts. This is most easily accomplished by placing the calcium phosphate composition in contact with a source of the patient's own bone forming cells. Such cells may be found in bone-associated tissue, blood or fluids, including exogenous fluids which have been in contact with bone or bone materials or regions, including the periosteum, cancellous bone or marrow. When used in conjunction with devices such as screws and pins, the introduction of which into bone is accompanied by breach of the periosteum and/or bleeding, no further seeding is required. For plates, which oppose only cortical bone, induction of a periosteal lesion which will contact the device is recommended. In yet other embodiments, it will be useful to surgically prepare a seating within the bone by removing a portion of cortical bone at the implant site. Bone forming cells harvested from the patient may be introduced into the graft to augment ossification. Use of non-autologous bone cells is also within the scope of the invention if the desired amount of bone regeneration occurs prior to host rejection of the bone forming cells. Thus, cells or tissues obtained from primary sources, cell lines or cell banks may all be useful in certain embodiments. See U.S. Pat. No. 6,132,463 to Lee et al., which is incorporated herein by reference.

Supplementary Material

The composite material of the present invention may be prepared by combining the calcium phosphate material, effervescent agent and biologically active agent with a selected supplementary material. The calcium phosphate may serve as the reinforcing material, the matrix or both. The calcium phosphate material in its initial hydrated form typically maintains a pH of about 6-7 and is therefore compatible with a wide range of additives without deleterious effect. The supplementary material is selected based upon its compatibility with calcium phosphate and the other components and its ability to impart properties (biological, chemical or mechanical) to the composite, which are desirable for a particular therapeutic purpose. For example, the supplementary material may be selected to improve tensile strength and hardness, increase fracture toughness, provide imaging capability, and/or alter flow properties, and setting times of the calcium phosphate material.

The supplementary material may be added to the calcium phosphate composition in varying amounts and in a variety of physical forms, dependent upon the anticipated therapeutic use. For example, the supplementary material may be in the form of solid structures, such as sponges, meshes, films, fibers, gels, filaments or particles, including micro- and nano-particles. The supplementary material itself may be a composite. The supplementary material may be a particulate or liquid additive or doping agent which is intimately mixed with the resorbable calcium phosphate. When intimately mixed with a PCA calcium phosphate material, the supplementary material may interfere on a macroscopic level with the cementing reaction. This may occur with the supplementary material coating a percentage of the cement particles, allowing a weak cementing reaction to occur with the coated particles. Alternatively, the liquid or solid may cause physical separation between the reactive species resulting in focal areas of cement formation (or granules). The supplementary material may serve as a matrix for the calcium phosphate, which is embedded or dispersed within the matrix. Alternatively, the calcium phosphate may serve as a matrix for the supplementary material, which is dispersed therein. The supplementary material may be applied as a coating onto a calcium phosphate body, for example, as a post-fabrication coating to retard resorption time or otherwise affect the bioceramic material properties. Lastly, the supplementary material may be coated with the calcium phosphate composition.

The supplementary materials are desirably biocompatible, that is, there is no detrimental reaction induced by the material when introduced into the host. In many instances, it is desirable that the supplementary material also be bioresorbable. The supplementary material may have an affinity for calcium, phosphate or calcium phosphates which will enhance the strength of the calcium phosphate/supplementary material interface. The affinity may be specific or mediated through non-specific ionic interactions. By way of example only, suitable bioerodible polymers for use as a matrix in the composite include, but are not limited to, collagen, glycogen, chitin, celluloses, starch, keratins, silk, nucleic acids, demineralized bone matrix, derivativized hyaluronic acid, polyanhydrides, polyorthoesters, polyglycolic acid, polylactic acid, and copolymers thereof. In particular, polyesters of αZhydroxycarboxylic acids, such as poly(L-lactide) (PLLA), poly(D,L-lactide) (PDLLA), polyglycolide (PGA), poly(lactide-co-glycolide) (PLGA), poly(D, L-lactide-co-trimethylene carbonate), and polyhydroxybutyrate (PHB), and polyanhydrides, such as poly (anhydride-co-imide) and co-polymers thereof are known to bioerode and are suitable for use in the present invention. In addition, bioactive glass compositions, such as compositions including $SiO_2$, $Na_2O$, $CaO$, $P_2O_5$, $Al_2O_3$ and/or $CaF_2$, may be used in combination with the calcium phosphate composition of the invention. Other useful bioerodible polymers may include polysaccharides, peptides and fatty acids.

Bioerodible polymers are advantageously used in the preparation of bioresorbable hardware, such as but not limited to intermedullary nails, pins, screws, plates and anchors for implantation at a bone site. The bioresorbable fiber may be in the form of whiskers which interact with calcium phosphates according to the principles of composite design and fabrication known in the art. Such hardware may be formed by pressing a powder particulate mixture of the calcium phosphate and polymer. Alternatively, the calcium phosphate matrix may be reinforced with PLLA fibers, using PLLA fibers similar to those described by Tormala et al., which is incorporated herein by reference, for the fabrication of biodegradable self-reinforcing composites (*Clin. Mater.* 10:29-34 (1992)).

Bioresorbable polymers may also be used in the preparation of bone glues or putties for use in load bearing situations. Supplementary materials may be added to the composite to increase compressibility and load-bearing properties of the bone glue. In particular, carbon fibers or other reinforcing fibers may be added to the composite. In the production of fiber-reinforced bone substitute glues, it may be advantageous to plasma etch the fibers to improve the quality and strength of the calcium phosphate/fiber interface. Calcium phosphate may also be hardened at 37° C., pulverized or otherwise fragmented, and mixed with known binders such as bone glues cements, fillers, plasters, epoxies, other calcium phosphates, or gels such as, but not limited to, calcium sulfate, alginate, collagen, or commercially available products such as Endobone (Merck), Hapset (Lifecore Biomedical), SRS® (Norian), BONESOURCE® (Leibinger), COLLOGRAFT® (Zimmer), OSTEOGRAF® (CereMed), and SIMPLEX® (Howmedica). For applications where hardened calcium phosphate will be dispersed within the binder substance, most often the binder will be prepared by methods known to the art and mixed with the particulate calcium phosphate in approximately equal volumes, although actual proportions will be varied in ways known to the art to produce compositions of desired consistency, workability and adherence.

In yet another embodiment, braided sutures, typically prepared from polyester, maybe coated with the calcium phosphate composition of the invention, to improve their biocompatibility. Coated sutures may be prepared by dipping the suture into a slurry containing the calcium phosphate material. The affinity of the suture for the calcium phosphate coating may be improved by surface treating either the suture, the calcium phosphate particle or both. Surface treatments include plasma etching and/or chemical grafting.

In other embodiments, a composite is provided comprising the calcium phosphate material and a non-resorbable or poorly resorbable material. Suitable non-erodible or poorly erodible materials include dextrans, polyethylene, polymethylmethacrylate (PMMA), carbon fibers, polyvinyl alcohol (PVA), poly(ethylene terephthalate)polyamide, bioglasses, and those compounds listed previously for use in bone glues or putties.

Another use is to permanently imbed useful objects, such as a pin or reinforcing mesh, into bone itself. The object serves as an anchor for the stable attachment to natural bone. This is particularly useful in the attachment of ligaments and tendons to bone. Objects comprising bioresorbable and ossifying calcium phosphate and a suitable non-resorbable hardware may be placed into a bone and further secured with additional calcium phosphate material or composite material in a bone glue formulation. The hardware then becomes embedded into the bone following reossification of the calcium phosphate material.

In yet another embodiment of the invention, a composition is prepared by blending the calcium phosphate or composite material with an additive which alters the resorption properties, setting time and/or flow characteristics of the composite. For example, silicone oil or other lubricating polymers or liquids may be added to the composite to improve the flow characteristics of the composite for delivery to the host by syringe. The lubricant is preferably biocompatible and capable of rapid leaching from the bone substitute material composite following solidification of the calcium phosphate composition in vivo. Suitable lubricants include, by way of example only, polymer waxes, lipids and fatty acids. Lubricants may be used in a concentration of about 0.1 to about 30 wt %.

The following examples detail presently preferred embodiments of the invention. Numerous modifications and variations in practice thereof are expected to occur to those skilled in the art upon consideration of these descriptions. Those modifications and variations are believed to be encompassed within the claims appended hereto. These examples do not in any way limit the invention.

The entire contents of all references, patents and published patent applications cited throughout this application are incorporated herein by reference.

EXAMPLES

All components utilized in these examples are pharmaceutical grade. The calcium phosphate component was the commercially available bone substitute material sold under the tradename CEREDEX® by Etex Corporation, 38 Sydney Street, Cambridge, Mass. 02139. The biologically active agent utilized was recombinant human bone morphogenetic protein-2 (rhBMP-2). The production and characterization of BMP-2 is described in detail in U.S. Pat. No. 5,013,649.

Example 1

Preparation of Calcium Phosphate Composition

A poorly crystalline amorphous calcium phosphate apatitic paste was prepared as described in U.S. Pat. No. 5,650,176, which is hereby incorporated by reference in its entirety herein, except that 20% by weight sodium bicarbonate was added to the amorphous calcium phosphate (ACP) powder precursor. The ACP was then hydrated with a limited amount of water to form a paste, which remained workable at room temperature for 20-30 minutes.

Example 2

In Vitro Implant Analysis

A calcium phosphate composition was prepared as described in Example 1. The hydrated paste was then injected into a saline bath at body temperature. The calcium phosphate material hardened into macrogranules under simulated in vivo conditions (i.e., 37° C.).

Example 3

Intramuscular Injection

A first calcium phosphate composition containing 20% by weight sodium bicarbonate was prepared as described in Example 1. A second calcium phosphate paste was prepared as described in U.S. Pat. No. 5,650,176, except that 29% by weight polyethylene glycol was added to the amorphous calcium phosphate (ACP) powder precursor. The two ACP compositions were then hydrated with a limited amount of water to form two pastes, both of which formed macrogranules of approximately 100-1000 microns upon explantation several hours post-injection. In addition (data not shown), granulation occurred after the injection of 20 µg rhBMP-2, delivered in either the calcium phosphate monolithic setting cement or the self-granulating calcium phosphate composition. The amount of bone induced at 21 days using rhBMP-2 delivered in the macrogranular (calcium phosphate) composition was significantly greater than the control material (monolithic cement); data not shown. Moreover, the local retention of rhBMP-2 delivered using the macrogranular calcium phosphate materials was significantly less than the control material (i.e., approximately 30% versus 75%; data not shown). The inventive macrogranular composition provides a faster release of the osteoinductive protein due to increased surface area available for osteoclast resorption of the matrix. This matrix resorption in turn releases soluble rhBMP-2 from the calcium phosphate material.

Example 4

Intrafibular Osteotomy Injection

A calcium phosphate composition containing 20% by weight sodium bicarbonate was prepared as described in Example 1. 20 µg rhBMP-2 was added to the resulting ACP composition, which was then hydrated with a limited amount of water to form a paste. 0.5 cc of the hydrated material was injected into a nonhuman primate fibular osteotomy. Granulation and dispersion of the macrogranules was evident after one day. In contrast, at one week post-injection, the standard calcium phosphate material without sodium bicarbonate (control) remained in a solid monolithic mass (data not shown).

Example 5

Nonhuman Primate Fibula Osteotomy

A calcium phosphate composition containing 20% by weight sodium bicarbonate (rhBMP-2/NaBSM20) was prepared as described in Example 4. The goal of this study was to determine the efficacy of a single percutaneous injection of rhBMP-2/NaBSM20 administered 7 days after surgery to accelerate fibula osteotomy healing in adult male cynomolgus monkeys. These results were compared to a previous study where the injection was made 3 hours after surgery (data not shown). Bilateral fibula osteotomies, stabilized with a small intramedullary pin, were created in 12 animals. One osteotomy in six animals was injected with 0.5 mL of 1.5 mg/mL rhBMP-2 per mL of NaBSM20 seven days after creating the osteotomy. The contralateral fibula osteotomy was left untreated as a surgical control. One osteotomy in the remaining six animals was injected with buffer/NaBSM20 without rhBMP-2 to serve as a carrier control. The contralateral osteotomy again served as an untreated surgical control.

Serial radiographs taken at weekly intervals after surgery revealed mineralized bone formation in the rhBMP-2/NaBSM treated osteotomies as early as 1 week after injection. By two weeks after injection there was considerable new bone formation visible radiographically. Bridging new bone callus across the osteotomy was present as early as 3-5 weeks after treatment (4-6 weeks after osteotomy). The osteotomies were healed radiographically by 7 weeks after treatment (8 weeks after osteotomy). There was no evidence of residual NaBSM carrier material at this time point. Evidence of new bone formation in the contralateral controls did not appear until around 3-4 weeks after injection (4-5 weeks after osteotomy). There was no radiographic evidence, of bridging callus or osteotomy healing at 7 weeks after treatment (8 weeks after osteotomy) in the contralateral surgical controls from the rhBMP-2/NaBSM treatment group. The radiographic appearance of the buffer/NaBSM treated and contralateral surgical controls in the second group of animals was similar to the contralateral surgical controls in the rhBMP-2/NaBSM treated group. There was still evidence of residual carrier in the buffer/NaBSM treated osteotomies at 7 weeks after injection (8 weeks after osteotomy).

Torsional mechanical strength of the rhBMP-2/NaBSM20 treated osteotomies at 8 weeks after osteotomy was significantly greater than the strength and stiffness of normal bone (1.58±0.40 vs 1.24±0.26 Nm). Torsional strength was also significantly greater in this group compared to the contralateral surgical controls (0.72±0.19 Nm) and the buffer/Na/BSM20 and contralateral surgical treated osteotomies of this group (0.87±029 and 0.74±0.21 Nm). There was no significant difference between torsional mechanical strength in the buffer/NaBSM20 osteotomies compared to the contralateral surgical control osteotomies from the same animals and compared to the surgical controls of the rhBMP-2/NaBSM animals. The untreated surgical control osteotomies approach mechanical strength of normal bone after about 14-16 weeks. Similar results were observed for osteotomy stiffness.

This study demonstrates a greater than 50% acceleration of osteotomy healing in response to injection of rhBMP-2/NaBSM20 seven days after creating the osteotomy. The appearance of new bone formation was much sooner than was observed in the rhBMP-2/NaBSM and rhBMP-2/aBSM osteotomies treated at 3 hours and 1 day after osteotomy in previous studies. The torsional mechanical strength was also greater in animals treated 7 days after osteotomy compared to 3 hr and 1 day treatment. Acceleration of osteotomy healing was around 30-40% when the treatment was administered at these two time points. Preliminary results indicate that accelerated osteotomy healing can also be achieved with treatment administered 2 weeks after creating the osteotomy. These results of these studies indicate that the combination or rhBMP-2/NaBSM significantly accelerates osteotomy healing when administered between 3 hours and 7 days after creating the osteotomy.

What is claimed is:

1. A method of treating a mammal having a dental defect comprising administering to the site of the dental defect an effective amount of a composition comprising at least one osteogenic protein, a calcium phosphate material as a carrier, and an effective amount of a material that liberates gas upon dissolution in vivo, wherein the at least one osteogenic protein comprises a member of the TGF-$\beta$ family.

2. The method of claim 1, wherein the at least one osteogenic protein comprises a heterodimeric osteogenic protein.

3. The method of claim 1, wherein the at least one osteogenic protein comprises BMP-2.

4. A method of imbedding an object into a bone of a mammal comprising placing an object comprising non-resorbable hardware into the bone and further securing the object with a composition comprising at least one osteogenic protein, a calcium phosphate material as a carrier, and an effective amount of a material that liberates gas upon dissolution in vivo, wherein the at least one osteogenic protein comprises a member of the TGF-$\beta$ family.

5. The method of claim 4, wherein the object is a pin or reinforcing mesh.

6. The method of claim 4, wherein the object provides an attachment site for a tendon or ligament.

7. The method of claim 4, wherein the at least one osteogenic protein comprises a heterodimeric osteogenic protein.

8. The method of claim 4, wherein the at least one osteogenic protein comprises BMP-2.

9. A method of improving biocompatibility of braided sutures comprising coating the braided sutures with a composition comprising at least one osteogenic protein, a calcium phosphate material as a carrier, and an effective amount of a material that liberates gas upon dissolution in vivo, wherein the at least one osteogenic protein comprises a member of the TGF-$\beta$ family.

10. The method of claim 9, wherein the braided sutures are dipped in a slurry.

11. The method of claim 9, further comprising surface treatment of the suture or the composition.

12. The method of claim 9, wherein surface treatment comprises plasma etching or chemical grafting.

13. The method of claim 9, wherein the at least one osteogenic protein comprises a heterodimeric osteogenic protein.

14. The method of claim 9, wherein the at least one osteogenic protein comprises BMP-2.

15. A method of treating a bone defect in a mammal comprising administering to the site of the bone defect an effective amount of a composition comprising at least one osteogenic protein, a calcium phosphate material a carrier, and an effective amount of a material that liberates gas upon dissolution in vivo, wherein the at least one osteogenic protein comprises a member of the TGF-$\beta$ family.

16. The method of claim 15, wherein administration of the composition results in a custom fit of the composition to the bone defect.

17. The method of claim 15, wherein the composition of claim 1 is pre-hardened outside the body, loaded with the biologically active agent and material that liberates gas upon dissolution in vivo, and implanted at a later time.

18. The method of claim 15, wherein the composition of claim 1 is seeded with bone forming cells.

19. The method of claim 18, wherein the cells are from an in situ bone lesion.

20. The method of claim 18, wherein the cells are autologous.

21. The method of claim 18, wherein the cells are heterologous.

22. The method of claim 15, wherein the at least one osteogenic protein comprises a heterodimeric osteogenic protein.

23. The method of claim 15, wherein the at least one osteogenic protein comprises BMP-2.

24. A method of osseous augmentation or regeneration in a mammal comprising administering, to the site where augmentation or regeneration is desired, an effective amount of a composition comprising at least one osteogenic protein, a calcium phosphate material as a carrier, and an effective amount of a material that liberates gas upon dissolution in vivo, wherein the at least one osteogenic protein comprises a member of the TGF-β family.

25. The method of claim 24, wherein the site of augmentation or regeneration is in osteopenic bone.

26. The method of claim 24, wherein the augmentation or regeneration is for a bone implant or prosthesis.

27. The method of claim 24, wherein the at least one osteogenic protein comprises a heterodimeric osteogenic protein.

28. The method of claim 24, wherein the at least one osteogenic protein comprises BMP-2.

* * * * *